US009121012B2

(12) United States Patent
Scott et al.

(10) Patent No.: US 9,121,012 B2
(45) Date of Patent: Sep. 1, 2015

(54) STAGED INOCULATION OF MULTIPLE CYANOBACTERIAL PHOTOBIOREACTORS

(71) Applicant: Algenol Biofuels Inc., Fort Myers, FL (US)

(72) Inventors: Brendan Scott, Fort Myers, FL (US); George Meichel, Fort Myers, FL (US); Jesse Phillips-Kress, Fort Myers, FL (US); Jessica Blanks, Fort Myers, FL (US)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 14/145,203

(22) Filed: Dec. 31, 2013

(65) Prior Publication Data

US 2014/0273175 A1 Sep. 18, 2014

Related U.S. Application Data

(60) Provisional application No. 61/852,169, filed on Mar. 15, 2013.

(51) Int. Cl.
| | |
|---|---|
| *C12M 1/12* | (2006.01) |
| *C12N 1/12* | (2006.01) |
| *C12N 1/20* | (2006.01) |
| *C12P 7/06* | (2006.01) |
| *C12P 7/14* | (2006.01) |
| *C12M 1/00* | (2006.01) |

(52) U.S. Cl.
CPC .................. *C12N 1/12* (2013.01); *C12M 21/02* (2013.01); *C12M 21/12* (2013.01); *C12M 23/58* (2013.01); *C12N 1/20* (2013.01); *C12P 7/065* (2013.01); *C12P 7/14* (2013.01)

(58) Field of Classification Search
IPC .............. C12N 1/12; C12M 21/02; Y02E 50/17
See application file for complete search history.

(56) References Cited

U.S. PATENT DOCUMENTS

| | | | |
|---|---|---|---|
| 6,306,639 B1 | 10/2001 | Woods et al. | |
| 6,699,696 B2 | 3/2004 | Woods et al. | |
| 7,770,322 B2 * | 8/2010 | Huntley et al. | ............. 47/1.4 |
| 7,794,969 B1 | 9/2010 | Reppas et al. | |
| 8,183,027 B2 | 5/2012 | Reppas et al. | |
| 8,268,601 B2 * | 9/2012 | Huntley et al. | ............. 435/166 |
| 2010/0304456 A1 | 12/2010 | Huntley et al. | |
| 2011/0217692 A1 | 9/2011 | Morgan et al. | |
| 2011/0287541 A1 | 11/2011 | Cuello et al. | |

FOREIGN PATENT DOCUMENTS

| | | |
|---|---|---|
| WO | WO/2011/094457 | 8/2011 |
| WO | WO/2012/000057 | 1/2012 |
| WO | WO/2012/101459 | 8/2012 |
| WO | 2014/145185 | 9/2014 |

OTHER PUBLICATIONS

Response to Office Action and inventor declaration dated Apr. 24, 2014 for corresponding U.S. Appl. No. 14/098,703.
Office Action dated May 13, 2014 for corresponding U.S. Appl. No. 14/098,703.
Office Action dated May 21, 2014 for corresponding U.S. Appl. No. 14/098,703.
Examiner Interview Summary dated Jun. 3, 2014 for corresponding U.S. Appl. No. 14/098,703.
Response to Office Action and inventor declaration dated Aug. 21, 2014 for corresponding U.S. Appl. No. 14/098,703.
Office Action dated Sep. 15, 2014 for corresponding U.S. Appl. No. 14/098,703.
Response to Office Action dated Nov. 17, 2014 for corresponding U.S. Appl. No. 14/098,703.
Advisory Action dated Nov. 24, 2014 for corresponding U.S. Appl. No. 14/098,703.
Notice of Appeal and Pre-Appeal Brief dated Dec. 12, 2014 for corresponding U.S. Appl. No. 14/098,703.
International Search Report and Written Opinion for corresponding International Application PCT/US2014/029903.
Corresponding U.S. Appl. No. 14/098,703, Published Dec. 2013.
Office Action dated Feb. 25, 2014 for corresponding U.S. Appl. No. 14/098,703.
Szita et al., (2005), "Development of a multiplexed Microbioreactor System for High Throughput Bioprocessing," Lab on a Chip 5:819-826.
Christenson, L., et al., (2011), "Production and Harvesting of Microalgae for Wastewater Treatment, Biofuels, and Bioproducts," Biotechnology Advances 29:686-702.
Deng, M.D. et al., (1999), "Ethanol Synthesis by Genetic Engineering in Cyanobacteria," Applied and Environmental Microbiology, 65:523-528.
Blanch, H.W., (2012), "Bioprocessing for Biofuels," Current Opinion in Biotechnology, 23:390-395.
Olguin, E.J., (2012), "Dual Purpose Microalgae-Bacteria-Based Systems That Treat Wastewater and Produce Biodiesel and Chemical Products Within a Biorefinery," Biotechnology Advances, 30:1031-1046.
Quinn, J.C., et al., (2012), "Nannochloropsis Production Metrics in a Scalable Outdoor Photobioreactor for Commercial Applications," Bioresource Technology, 117:164-171.

* cited by examiner

*Primary Examiner* — Ralph Gitomer
(74) *Attorney, Agent, or Firm* — Lawrence B. Ebert; Suzanne G. Jepson

(57) ABSTRACT

A method of rapid simultaneous inoculation of cyanobacteria to multiple commercial-scale closed photobioreactors for the production of a target molecule such as ethanol.

23 Claims, 6 Drawing Sheets

STAGED INOCULATION OF MULTIPLE CYANOBACTERIAL PHOTOBIOREACTORS

CROSS-REFERENCE TO RELATED APPLICATIONS

This application claims the benefit of U.S. Provisional Patent Application Ser. No. 61/852,169, filed Mar. 15, 2013, the disclosure of which is incorporated herein by reference.

STATEMENT REGARDING FEDERALLY SPONSORED RESEARCH

This invention was made in part with United States government support under the Department of Energy grant number DE-EE0002867. The government has certain rights in this invention.

REFERENCE TO SEQUENCE LISTING

Not Applicable.

TECHNICAL FIELD

This invention relates to methods of scaling to commercial production closed bioreactors, and, in particular, methods of rapid simultaneous inoculation of multiple commercial-scale closed photobioreactors. The process described herein is preferably directed to the use of cyanobacteria to produce target chemical products in photobioreactors.

BACKGROUND OF INVENTION

Cyanobacteria form a phylogenetically coherent group of gram-negative prokaryotes that are capable of oxygenic photosynthesis, wherein their photosystems PSI and PSII extract and transfer electrons from water molecules to electron acceptors and generate oxygen as a co-product. They are capable of fixing carbon from $CO_2$ under aerobic conditions.

As photoautotrophic organisms, the rates of photosynthesis and growth of cyanobacteria are directly affected by the physical parameters of the environment.

In the wild, the competitive success of cyanobacteria depends on a continual fine-tuning of growth rate in order to exploit the changing nutritional environment. To cope with depleted nutrients and exploit those that are plentiful, the cyanobacteria undergo transitions from exponential to arithmetic (linear) growth into non-growth (stationary) physiological states.

The duration of the exponential and linear growth phase in culture depends upon the size of the inoculum, starting density of the inoculum, growth rate, environmental conditions, and capacity of the medium to support microbial growth. Cyanobacterial growth does depend on light intensity. The dependence on external light intensity is impacted by culture density.

It has been reported by Foster that wild cyanobacteria grow optimally in the range of 15-75 $\mu E\ m^{-2}\ s^{-1}$ and batch cultures progress from a lag phase into an exponential growth phase. This is typically followed by a period of linear growth that continues until the culture reaches the non-growing stationary phase. Linear growth in bacteria occurs when there are perturbations in the environment such that a critical nutrient is regulated arithmetically. In cyanobacteria, linear growth is most often associated with light limitation caused by self-shading of cells as cultures reach a certain cell density J. S. Foster, et al., Arch. Microbiol, (2007) 187:265-279. The optimal light range may be broader than indicated by Foster, such as 15-300 $\mu E\ m^{-2}\ s^{-1}$.

In 1999, Deng and Coleman disclosed the introduction of new genes into the *Cyanobacterium Synechococcus* PCC 7942 to create a novel pathway for fixed carbon utilization which created the target chemical product ethanol. M.-D. Deng and J. R. Coleman, Appl. Envir. Microbiology (1999) 65: 523-528. Related patents are R. P. Woods, et al. U.S. Pat. No. 6,306,639 and U.S. Pat. No. 6,699,696. Other target chemical products have been identified; see for example, U.S. Pat. No. 7,794,969 and U.S. Pat. No. 8,183,027.

In the production of target chemical products, such as ethanol, from microorganisms, such as cyanobacteria, an inoculum of the microorganism is needed so as to provide a population of such microorganism, suitable for scaling up to levels amenable to commercial scale production. In the case of specialty chemicals, produced in low amounts, this inoculum might be cultured in a vessel so that the cell density increases to a cell density suitable for reaching a production level that meets overall productivity metrics. [See for example PCT/US2011/022790, MICROORGANISM PRODUCTION OF HIGH-VALUE CHEMICAL PRODUCTS, AND RELATED COMPOSITIONS, METHODS AND SYSTEMS; see separately Example 1 of PCT/GB2012/050194] The production of other target molecules from cyanobacteria are discussed in Ruffing et. al., Physiological effects of free fatty acid production in genetically engineered *Synechococcus elongatus* PCC 7942, Biotechnology and Bioengineering (2012) 109:2190-2199; and in V. H. Work, et al., Biocommodities from photosynthetic microorganisms, Environmental Progress & Sustainable Energy (2013) 32:989-1001. In the case of commodity chemicals, such as biofuels, inoculum scale-up might proceed in several stages.

In the case of inocula to create cultures for open systems, published US application 20100304456 lays out some guidelines:

It is preferred that (1) the amount of biomass provided by the Closed Systems to inoculate the Open Systems should be equal to more than 5% of the carrying capacity of the aggregate Open Systems; (2) the growth rate of the species being cultivated is greater than approximately one and a half doublings per day (i.e. cell biomass doubles about every 16 hours); and that (3) no culture be maintained in any Open System for a period of more than 5 days. The combination of these three limitations assures that, under any circumstances, the culture should attain a biomass of the desired microbe that is equal to at least approximately 90% of the carrying capacity in 5 days or less. This is important for several reasons. First, a culture that is inoculated at a relatively high cell concentration (i.e. greater than 5% of carrying capacity) will dominate the medium compared to any unwanted cells that may have inadvertently been introduced. Second, because most species grow at rates substantially less than 1 doubling every 16 hours (1.5 doublings per day), a species that is capable of growing this rapidly will outpace most potential competitors. Third, the combination of the large inoculum (greater than 5% of carrying capacity) and high growth rate (greater than 1 doubling every 16 hours) assures that, within 5 days, the total biomass will be very near carrying capacity. These conditions are important to (1) reducing the risk of contamination, and (2) promoting the production of total biomass or the biosynthesis or production of oil. First, a potential contaminant would have to have a large inoculum and would have to grow more rapidly than the desired species to dominate the culture medium within 5 days. Second, oil production in particular is favored in cultures that are near carrying capacity because resources become limiting to growth once the culture passes 50% of carrying capacity. By limiting resources favorable to growth, one generally stimulates the biosynthesis of oil.

Paragraph 81 of US 20110217692 shows the risks of contamination.

Paragraph 82 of US 20110287541 discusses amounts stored for use as inocula.

Example 4 of PCT/AU2011/000829 describes inoculation of a large bioreactor with a volume of inoculum, followed by growth, and followed by further dilution.

Earlier art mentions the preparation of inocula ultimately for use in open, rather than closed, systems. For example, H. W. Blanche, Current Opinion in Biotechnology (2012) 23:390-395; E. Olguin, Biotechnology Advances (2012) 30:1031-1046; J. Quinn, Bioresource Technology (2012) 117: 164-171; I. Christenson, Biotechnology Advances (2011) 29:686-702 [discussing Cellana].

The present invention is directed to the creation of inocula suitable for introduction into closed bioreactor systems. The present invention provides a method for rapid scale-up of inoculum by monitoring of optical density, and control thereof. An embodiment of the invention permits the method to proceed by minimizing exposure of the inoculum to ambient air.

In another embodiment, a plurality of photobioreactors connected in parallel can be inoculated from a series of scale-up cultures. In a further embodiment, the culture is transferred rapidly and evenly to the plurality of photobioreactors. In a further embodiment, the process is performed so that the photobioreactor culture is axenic or substantially axenic.

SUMMARY OF INVENTION

An aspect of the present invention is a method for the staged growth of inoculum.

In an aspect of the invention, a process for inoculating a plurality of closed photobioreactors connected in parallel is provided, each photobioreactor having a volume from about 10 liters to about 100 liters, with a cyanobacteria genetically enhanced for formation of a target molecule, having the steps of:
  a. growing an inoculum culture of the genetically enhanced cyanobacteria in a first container to an $OD_{750}$ of from about 1.0 to about 10.0 in a volume of from about 1 liter to about 10 liters of pre-sterilized medium;
  b. transferring the inoculum culture in a sterile manner under pressure without exposure to atmosphere from the first container to a pre-sterilized second container;
  c. growing the inoculum culture in the second container to an $OD_{750}$ of from about 1.0 to about 10 in a volume of from about 20 liters to about 100 liters of pre-sterilized medium;
  d. transferring the inoculum culture in a sterile manner under pressure without exposure to atmosphere from the second container to a pre-sterilized third container;
  e. growing the inoculum culture in the third container to an $OD_{750}$ of from about 2.0 to about 10 in a volume of from about 200 liters to about 1,000 liters of pre-sterilized medium; and
  f. transferring the inoculum culture in a sterile manner at a pressure of from about 5 to about 50 psi without exposure to atmosphere from the third container and a sterilized nutrient solution, to a plurality of pre-sterilized photobioreactors having a pre-sterilized liquid, where said pre-sterilized photobioreactors have inlet tubing having a drip emitter and are configured in parallel from the third container, where said drip emitter controls the culture flow so that each of the photobioreactors connected in parallel is inoculated at a substantially similar flow rate.

The inoculum culture can be axenic. The volume can be selected to obtain a starting cell density of the photobioreactors connected in parallel can be, for example, from about $OD_{750}$ of 0.01 to about 0.5. The starting cell density of the photobioreactors connected in parallel can be from about $OD_{750}$ of 0.01 to about 0.5. The inoculum culture can be grown, for example, to a cell density of about 2 to about 4 $OD_{750}$. The number of photobioreactors connected in parallel that are inoculated from one third container can be, for example, from about 25 to about 2,000. Each of the photobioreactors connected in parallel can have, for example, a final culture volume of about 18 to about 60 liters. The closed photobioreactors can be, for example, vertical bioreactors. The medium can be, for example, a fresh water cyanobacterial medium, a brackish water cyanobacterial medium, or a salt water cyanobacterial medium. The target molecule can be, for example, ethanol. At least one of the transfers can occur, for example, when the inoculum is in an exponential phase of growth, or in a linear phase of growth.

In another aspect of the invention, a process for inoculating a plurality of closed photobioreactors connected in parallel is provided, each photobioreactor having a volume from about 10 liters to about 500 liters, with a cyanobacteria genetically enhanced for formation of a target molecule, having the steps of growing a first inoculum culture of said genetically enhanced cyanobacteria in a first container having a volume of from about 1 liter to about 10 liters to an $OD_{750}$ of about 1.0 to about 10.0; and transferring in a sterile manner said first inoculum culture under pressure without exposure to atmosphere, to a sterilized second container of a larger size, and adding a volume of sterile medium to create a second inoculum culture of $OD_{750}$ between 0.04 and 0.5, and growing said second inoculum culture to an $OD_{750}$ of about 1.0 to about 10; and repeating to obtain sufficient volume to fill the plurality of closed photobioreactors.

In yet another aspect of the invention, a process for inoculating a plurality of closed photobioreactors connected in parallel is provided, each photobioreactor having a volume from about 10 liters to about 500 liters, with a cyanobacteria genetically enhanced for formation of a target molecule, having the steps of:
  a. determining conditions for growing the enhanced cyanobacteria in the exponential growth phase;
  b. growing a first inoculum culture of said genetically enhanced cyanobacteria in the exponential growth phase in a first container having a volume of from about 1 liter to about 10 liters;
  c. transferring in a sterile manner said first inoculum culture under pressure without exposure to atmosphere, to a sterilized second container of a larger size, in the presence of a volume of sterile medium to create a second inoculum culture of $OD_{750}$ between 0.04 and 0.5, and growing said second inoculum culture to an $OD_{750}$ of about 1.0 to about 10;
  d. transferring the second inoculum culture of OD 1 to 10 to a container of larger size having sterile liquid to create a third inoculum of $OD_{750}$ between 0.04 and 0.5 and growing the third inoculum to an $OD_{750}$ of about 1.0 to about 10; and
  e. transferring the third inoculum culture to each of a plurality of closed photobioreactors connected in parallel; where the enhanced cyanobacteria form a target molecule within the closed photobioreactors.

An embodiment of this system is given in FIG. 6.

Figure 1:
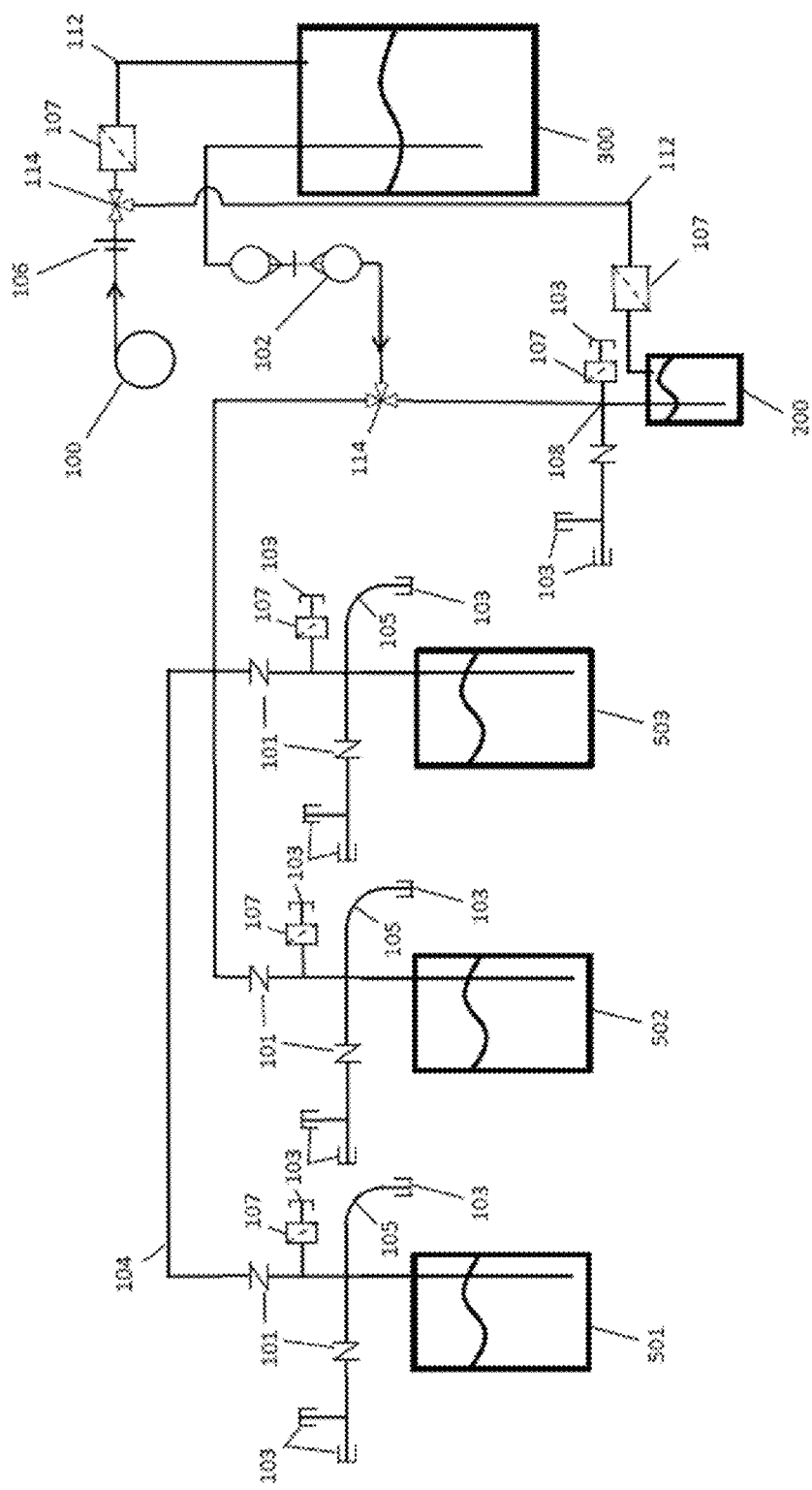
FIG. 1. An embodiment of the inoculum transfer procedure.
Figure 2:
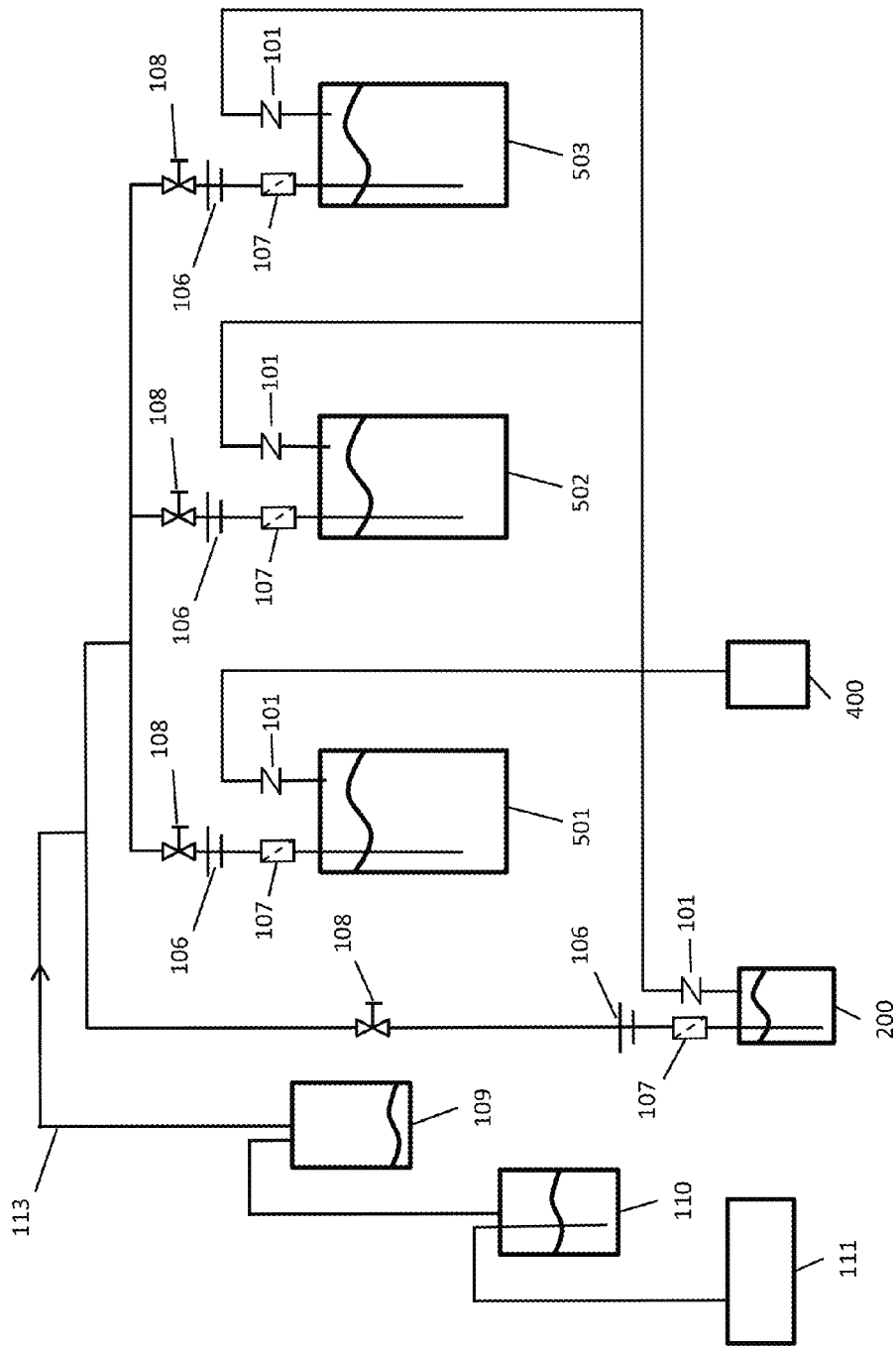
FIG. 2. An embodiment of the inoculum transfer procedure.
Figure 3:
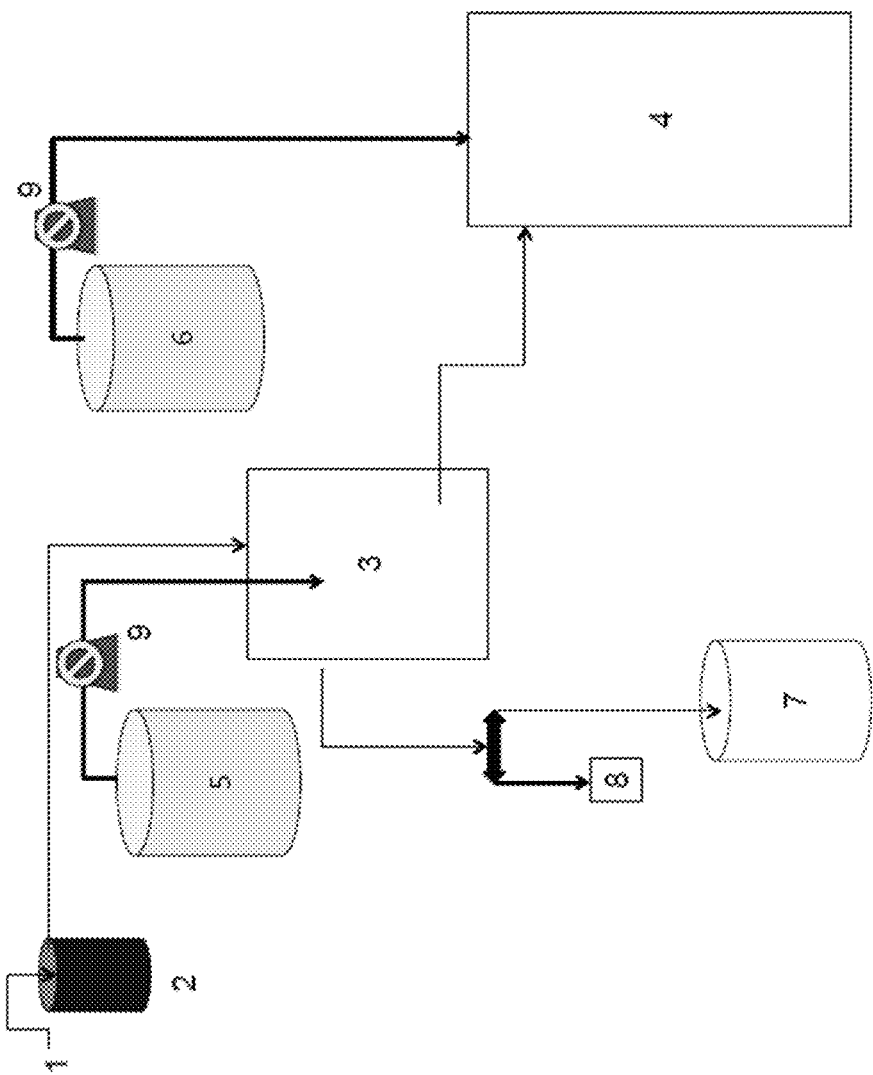

The numbered figure elements for FIGS. 1 and 2 are:
- 100: Air Pump
- 101: Check Valve
- 102: Quick Disconnect Coupling
- 103: Tubing Cap
- 104: Culture/Media filled line
- 105: ⅜" Santoprene Line to 80 L Inoculum bag
- 106: Luer Lock Air Pump Connection Fitting
- 107: 2 Micron Filter
- 108: Ball Valve
- 109: Liquid Trap
- 110: Humidifier
- 111: $CO_2$ Delivery
- 112: Air Filled Line
- 113: $CO_2$ Delivery Line
- 114: 3 way valve
- 200: 1 L Vessel
- 300: 20 L Nutrient Carboy
- 400: Exhaust Trap
- 501; 502; 503 etc.: 5 L Vessel FIG. 3. Schematic layout of inoculum embodiment. The numbered figures elements for FIG. 3 are:
1: Air inlet to pressurize vessel
2: 1 L culture with 500-900 ml culture volume
3: Large scale up vessel 1 (20 L, 80 L, or 500 L vessel)
4: Large scale up vessel 2 (80 L, 500 L, or inoculated PBR)
5: Media 1 (typically 20 L carboy with seawater and nutrients) to fill #3
6: Media 2 (typically 20 L carboy with seawater and nutrients) to fill #4
7: Overflow waste (if necessary)
8: Sample port
9: Peristaltic pump for better control on transfer without adding pressure to system

3 (paragraph 23) can be operated continuously to maintain an OD of 1.0 or lower. If culture reached full capacity, overflow can be turned over to new vessel (i.e., #4) or can be wasted in dump container (#7).

Figure 4:
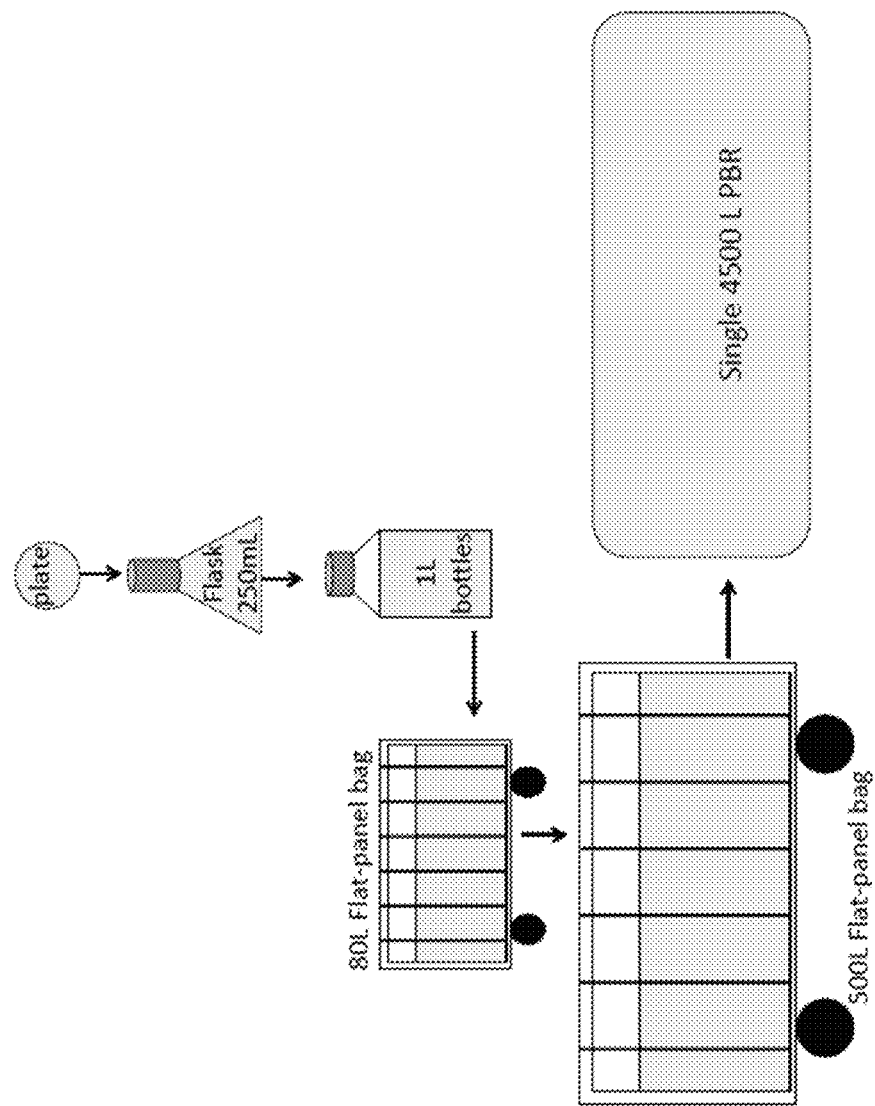

FIG. 4. Schematic layout showing scale-up to 4,500 liter bioreactor.

Figure 5:
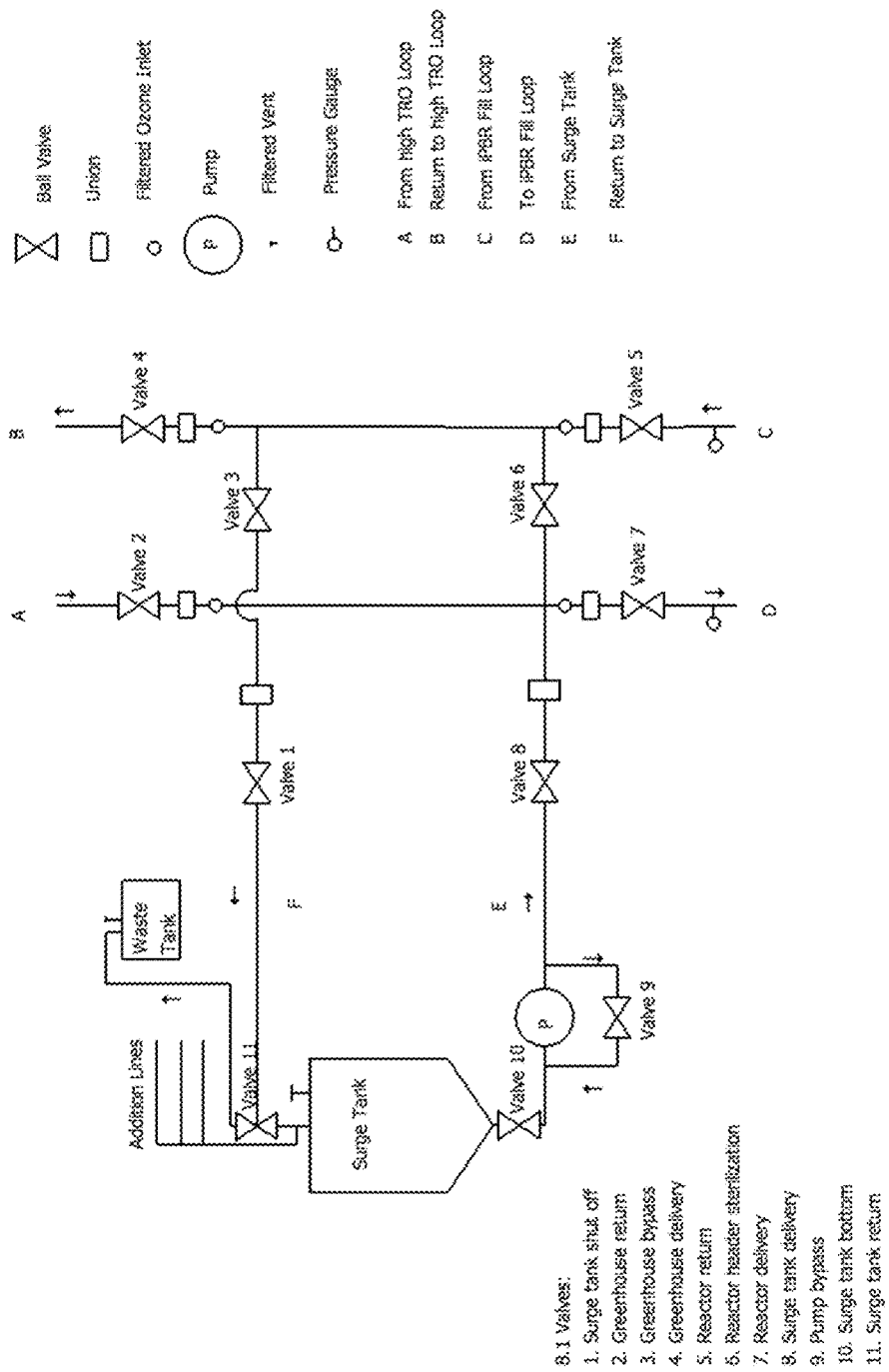

FIG. 5. Schematic layout of inoculum embodiment showing surge tank.

Figure 6:
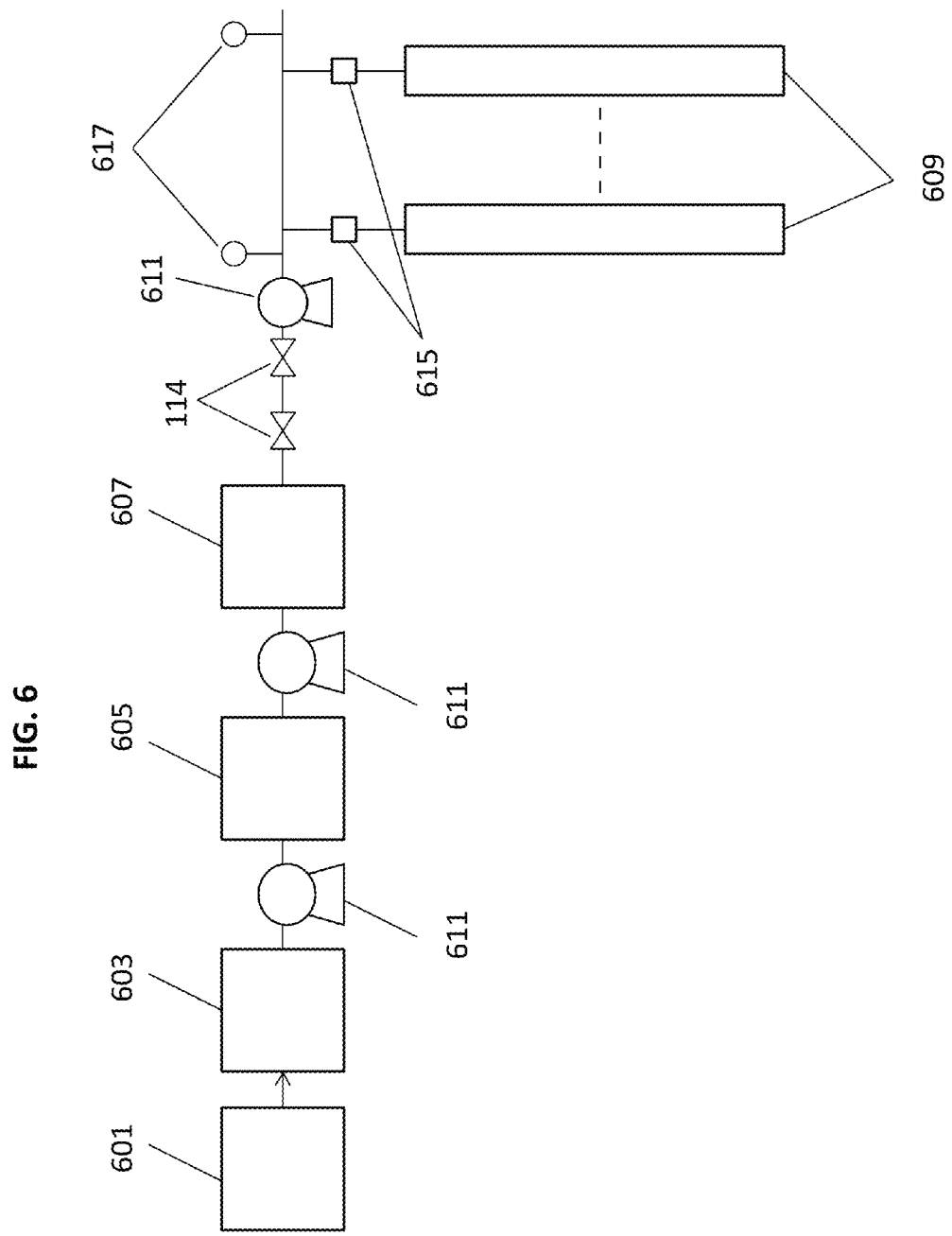

FIG. 6. Schematic layout of scale-up to large inoculum container, then transfer to a plurality of photobioreactors. The various sized containers, connecting tubing, pumping systems, and pressure compensation flow control devices (such as drip emitters) are shown.

The numbered figure elements for FIG. 6 are:
- 114: 3-way valve
- 601: Initial flask or vessel
- 603: First scale-up container
- 605: Second scale-up container
- 607: Third scale-up container
- 609: Plurality of photobioreactors connected in parallel
- 611: Pump
- 615: Pressure compensation flow control device (such as a drip emitter)
- 617: Gauge

DETAILED DESCRIPTION OF THE INVENTION

The axenic scale-up to large plots of photobioreactors (such as 1,000 or more) can have numerous logistical complications, such as possible contamination, sterilization of tubing and connection devices, sterilization of medium, multiple connections (each raising the risk of contamination of the system) along with issues related to the axenic transfer of the culture. Additionally, it is possible that large amounts of inoculum culture are forced to wait for an extended period of time in non-optimal conditions (such as high temperature, lack of mixing, poor gas exchange, poor light conditions) prior and during the transfer to the large-scale photobioreactors, which is likely to lower growth and productivity of the final photobioreactors. Further, the inoculum process can be time consuming and costly due to the additional personnel that would be needed for the process.

Accordingly, a process has been developed that enables large amounts of culture to be scaled-up and transferred to a plurality of photobioreactors. In an embodiment, the process results in multiple axenic or substantially axenic photobioreactors, each having a similar starting cell density. Further, the final transfer can occur rapidly. For example, 400 photobioreactors can be inoculated in about 30 minutes.

DEFINITIONS

As used herein, the term "about" means approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) within a confidence interval of 90% or 95%.

As used herein, the term "organism" is used to refer to any species or type of microorganism, including but not limited to bacteria, yeasts and other fungi. As used herein, the term "antimicrobial" is used in reference to any compound which inhibits the growth of, or kills microorganisms.

The terms "axenic" and "pure culture" refer to a culture that contains cells that are all members of the same species or strain of organism.

The term "substantially axenic" refers to the condition in which one main organism is present, but the culture may be contaminated with a small amount (such as less than 0.01%, or 0.1%) of another organism. Preferably, the cyanobacterial culture is axenic. However, this is often difficult to achieve on a large scale basis, in an outdoor environment. Thus, in an embodiment, the cyanobacterial culture is substantially axenic—that is, a contaminant is present at very low levels, but there is no significant effect on cyanobacterial cell growth or product production.

The term "sterile" means free from living microorganisms. Thus, conventional sterile procedures or other effective procedures for sterilization may be used to insure that the culture medium, tubing and connection devices, containers, photobioreactors, pumps, and valves, are sterile or substantially sterile.

The term "substantially sterile" means substantially free from living microorganisms. For example, if a sterilization process removes all but about 0.001%, 0.01%, or 0.1% of the contaminants, it can be considered, in some situations, "substantially sterile".

The term "pre-sterilized" means that the solution or object has been previously sterilized prior to use.

The term "in a sterile manner" as used herein refers to manipulations performed on sterilized or axenic liquids or objects so that they remain contaminant free. This can also be referred to as "sterile technique". This may include, for example, techniques such as using a sterile laminar hood to transfer medium from one container to another, heat-treating or sterilant-treating edges of containers prior to transfer, and touching a culture (such as a plate) with only pre-sterilized tools. Preferably, an axenic culture that is transferred to another container "in a sterile manner" will remain axenic (contaminant free) when present in the new container.

The term "contaminant test medium" refers to any material which supports the growth or replication of at least one potential contaminating microorganism in the cyanobacterial culture. These types of media are often prepared from basal media such as nutrient broth or peptone water. The term "contaminant test medium" may also be used in reference to solid plated media, such as a CC broth-based solid medium which supports the growth of microorganisms. Also included within this definition are semi-solid and liquid microbial growth media such as CC broth.

The term "streaking" shall be understood to mean a method of inoculation of the surface of a solid medium such that, during subsequent incubation, individual bacterial colonies (rather than confluent growth) develop on (at least) part of the medium surface.

As used herein, the term "inoculum" refers to an axenic or substantially axenic culture of cyanobacteria that is to be used to start a new culture of lower density and larger volume. An amount of inoculum is mixed with an amount of cell medium, and a new cell culture is grown.

The term "log phase growth" refers to the growth phase of cyanobacteria after the initial "lag phase" when the cells are multiplying exponentially by cell division. This can also be termed an "exponential growth phase".

The term "stationary phase" refers to the phase of growth after log phase where growth is attenuated, which can be caused by depletion or accumulation of products.

The term "linear phase" refers to the phase of growth after log phase but prior to stationary phase. Cell growth starts to slow down at this stage, but hasn't stopped. Nutrient limitation and light limitation are common causes of the initiation of this growth phase from the exponential phase of growth.

As used herein, the term "growth" is defined as expansion of the culture, i.e. increase of number of organisms in the culture, over a defined period of time.

As used herein, the term "$OD_{750}$" refers to the combination of the absorbance and the scattering of light having a wavelength of 750 nm. It is generally understood that while both absorbance and the scattering of light contribute to the OD, the scattering of light is the dominant factor for cyanobacterial cultures. The measurement is an estimate of cyanobacterial cell density.

The term "biomass" as used herein refers to a mass of living or biological material and includes both natural and processed.

The term "culturing" as used herein refers to incubating a cell or organism under conditions wherein the cell or organism can carry out biological processes.

The terms "culture medium" and "aqueous medium," as used herein in reference to the growth of cyanobacteria, refer to an aqueous medium designed to support the growth of cyanobacterial cells. An aqueous medium can be, for example, a natural water source such as a river, stream, lake, brackish water at the boundary between marine water and freshwater environment, or a marine water source. Aqueous medium, either fresh water or marine, can also be obtained from a well.

As used herein, the term "BG-11" means a standard cultivation medium for cyanobacteria that is well known to those of skill in the art. BG-11 contains all of the nutrients required for growth of many species of cyanobacteria. BG-11 is sold by, for example, Sigma-Aldrich Co. LLC as the product "Cyanobacteria BG-11 Freshwater Solution" under SKU C3061. "MBG-11" ("Marine BG-11") additionally contains NaCl, either from seawater, brackish water, or from salt addition to the medium to approximate the level that would be present in seawater. In an embodiment, NaCl is added to a level that is higher than that of seawater.

As used herein, the term "photobioreactor" means a device or system used to support a biologically active environment for the cultivation of photosynthetic microorganisms. A photobioreactor of the present invention may be constructed of translucent materials that permit penetration of light, or may otherwise incorporate a light source to provide photonic energy input for an aqueous culture of photosynthetic microorganisms contained therein. A photobioreactor of the present invention may be closed or semi-closed against the exchange of gases and contaminants with the outside environment. A photobioreactor of the present invention may be constructed from a flexible film or from a rigid film.

As used herein, the term "flexible film" means a continuous polymeric material or coating that is not structurally self-supporting, and preferably is at least partially translucent. Non-limiting examples of materials that can be used in flexible films suitable for use with the present invention are polyolefins, polyesters and vinyl copolymers thereof, including polyethylene, polypropylene, nylon and polyvinyl chloride.

The photobioreactor may be made of rigid materials such as extruded plastic, molded plastic domes, or plastic sheets or panels, or flexible materials, such as plastic film, or a combination of flexible and rigid materials. It may include framing members to impart strength or form to materials such as plastic extrusion, panels, or film that would otherwise have inadequate mechanical properties to create the desired structure.

The photobioreactor may be fabricated from any material, including glass, but preferably a plastic that has the optical clarity to permit photosynthesis and can withstand long-term UV radiation exposure and exposure to corrosive saltwater, heat and cold, and expansion and contraction. Glass, and opaque or translucent plastics may also be used, as long they meet the needs of the photoautotrophic organisms to be grown in the system. Any person skilled in the art of thermoplastics can specifically design a plastic, or plastic mix which can be used for the photobioreactor tube. Virgin resins may be used to manufacture the tubes, but since cost is a likely significant factor, recycled plastics are preferred. A few of the particular plastics can include High Density Polyethylene (HDPE), PolyethyleneTerephthalate (PET), acrylic, Lucite, polypropylene and polycarbonate, as discussed in U.S. Pat. No. 8,586,353. The desired life-span of the photobioreactor is a factor in the decision of the type of material to use.

The photobioreactor is preferably or transparent or translucent or at least partially translucent. As used herein, "partially translucent" should be understood as permitting sufficient passage of light, particularly sunlight, into the photobioreactor to enable photosynthesis by photoautotrophic organisms within the photobioreactor.

As used herein, the term "translucent" means allowing light to pass through, with or without scattering of photons.

As used herein, the term "thermoplastic" means a continuous polymeric material or coating that is rigid and substantially structurally self-supporting, and preferably is at least partially translucent. Non-limiting examples of thermoplastics suitable for use with the present invention are polycarbonate and polymethyl methacrylate.

As used herein, the term "light path" means the distance between the inner surfaces of opposing walls in a photobioreactor.

As used herein, the term "sparging" means a process whereby a gas is bubbled through a liquid.

Methods of Inoculum Scale-Up to a Plurality of Photobioreactors Connected in Parallel Although contamination with other bacteria or other organisms may not be a problem for some types of algal or cyanobacterial cultures, the use of cyanobacteria for the production of ethanol, which can be quickly consumed by contaminants in the culture, generally requires a contamination free or at least a low contamination level culture in order to produce high amounts of product.

To alleviate these issues, a method has been developed to inoculate multiple outdoor commercial-scale photobioreactors with genetically enhanced cyanobacteria in a relatively quick, convenient, and preferably axenic manner. The cells are grown from an initial plate, to a flask, and then to successively larger inoculum containers, using axenic culture methods (autoclaving, use of a laminar flow hood, etc.) as described herein. In an embodiment, an axenic culture is sequentially transferred to grow in a container that has a size of from about 1 to 10 liters, then the culture is axenically transferred to a container having a size of about 20 to about 100 liters, then to a container having a size of about 100 to 1,000 liters. This 100 to 1,000 liter container is grown to an $OD_{750}$ of from about 2.0 to about 10.0. This culture is then axenically distributed to multiple pre-sterilized transparent or translucent photobioreactors, where the compound of interest (such as ethanol) can then be synthesized and eventually collected.

In an embodiment, the plurality of photobioreactors can be inoculated substantially simultaneously. In an embodiment, the transfers occur in a sterile manner, or in a substantially sterile manner. This inoculation of the plurality of photobioreactors can occur within 30 minutes to one hour. In an embodiment, about 400 photobioreactors are inoculated in about 30 minutes.

The number of photobioreactors that receive the inoculum can be chosen as needed depending on the volume and cell density of inoculum, the initial cell density that is desired in the plurality of photobioreactors, pump and tubing requirements, sterilization requirements, etc. The inoculum container can be delivered, for example, to 2, 10, 25, 50, 100, 400, 500, 1,000, 1,500, 2,000, 3,000, or more photobioreactors. In an embodiment, the inoculum is delivered to a large land area of photobioreactors, such as 1 acre, 10 acres, 50 acres, 100 acres, 1,000 acres, or more.

For optimal culture growth, a culture is kept under exponential growth ("log phase") throughout the scale-up process. It is preferable to start each stage of the scale-up process with a culture having a high enough cell density to prevent a significant "lag phase" due to a low cell density of the newly transferred cells.

It is also preferable that the transfer to each subsequent stage takes place before the culture reaches stationary phase. Otherwise, there may be a significant lag phase once the culture placed in the new medium. Accordingly, in an embodiment, the $OD_{750}$ of the cells to be transferred is chosen so that it is at a high enough to allow a suitable $OD_{750}$ of the next dilution, but not high enough to be at stationary phase. Preferably, the cells to be transferred are in an exponential phase of growth. The cells can also be in an early linear phase, or a linear phase of growth. Each time the inoculum is transferred to a larger scale-up container and diluted with the appropriate amount of sterile medium, it will have a new lower cell density (and, accordingly, a lower $OD_{750}$).

The initial transfer to the first scale-up container can be performed by pouring the axenic culture into the container (filled with sterile medium) using sterile techniques inside of a laminar flow hood, if desired, rather than by using a pump.

While smaller-volume culture transfers early in the process can be done by carefully pouring from one container to another in a laminar flow hood or by use of sterile tubing set at a height-difference to allow gravimetric flow, the later scale up stages typically utilize a pumping system. The pump 611 can be, for example, a diaphragm pump or a peristaltic pump. Each of the pumps can be of the same type, or can be different types. Preferably, the chosen pumps are capable of being sterilized multiple times without damage.

Additionally, the method evenly distributes the inoculum, so that each of the multiple photobioreactors has a similar starting cell density. In an embodiment, the multiple photobioreactors are inoculated in a substantially simultaneous manner. In yet another embodiment, a plurality of photobioreactors, such as 200, 400, 1,000 or more, can be inoculated within 30 minutes to an hour.

A schematic diagram of a process of inoculation to a final plurality of photobioreactors is shown in FIG. 6. In an embodiment, the transfer from each scale-up container to the final plurality of photobioreactors occurs substantially as follows. Axenic culture is placed in the initial flask or vessel 601 containing sterile medium, and then grown up to a suitable cell density.

The inoculum grown in this initial vessel is then transferred to a first scale-up container 603 containing an appropriate amount of sterile medium and grown up to a suitable cell density. In an embodiment, the first scale-up container has a volume from about 1 liter to about 10 liters. In a further embodiment, the first scale-up container has a volume of about 5 liters.

The inoculum grown in the first scale-up container is then transferred to a second, larger sized scale-up container 605 containing an appropriate amount of sterile medium and grown to a suitable cell density. In an embodiment, the second scale-up container has a volume from about 20 liters to about 100 liters. In a further embodiment, the second scale-up container has a volume of about 80 liters.

To demonstrate how the dilution of the culture with the next larger stage container affects the $OD_{750}$, a 50 liter volume of the culture from the above-described second container having an $OD_{750}$ of about 10, once transferred to a 500 liter container with the appropriate amount of medium, would be diluted to an $OD_{750}$ of about 1. Similarly, a 20 liter culture from the above-described second container, grown up to a density of 2, then transferred to a 200 liter container with the appropriate amount of medium, would be diluted to an $OD_{750}$ of about 0.2.

This vessel is then transferred to a larger third scale-up container 607 containing sterile medium and grown to a suitable cell density. In an embodiment, the third scale-up container has a volume from about 200 liters to about 1,000 liters. In a further embodiment, the second scale-up container has a volume of about 500 liters.

When the culture in the third scale-up container 607 reaches a suitable cell density, it can be transferred to the plurality of photobioreactors 609 connected in parallel. Two three-way valves 114 allow for the tubing connections to be sterilized. A pressure of flow gauge 617 can be used to monitor the flow of inoculum to the photobioreactors. In an embodiment, each of the plurality of photobioreactors has a volume from about 18 to about 60 liters. In an embodiment, each of the plurality of photobioreactors has a starting optical density of about 0.01 to about 0.5 $OD_{750}$. In an embodiment, each of the plurality of photobioreactors is a vertical photobioreactor. In an embodiment, the number of photobioreactors that are inoculated is from about 100 to about 1,000. In a further embodiment, the number of photobioreactors that are inoculated is about 400.

In yet another embodiment, the distribution process to each of the photobioreactors (609) occurs substantially evenly, whether the photobioreactor is close to the inoculum or relatively far away from the inoculum container. Inoculated photobioreactors connected in parallel preferably have a variation in initial $OD_{750}$ of less than 5%.

Thus, in an embodiment of the invention, axenic cyanobacterial inoculum is sequentially scaled-up to a large inoculum container that is then evenly distributed to a plurality of photobioreactors, preferably in a simultaneous manner, so that each of the photobioreactors has a substantially similar starting cell density. This similarity of cell density is difficult to obtain when using serial inoculation to multiple photobioreactors.

The cell density of the inoculated plurality of photobioreactors can be adjusted as desired. A low cell density inoculum (such as, for example, an $OD_{750}$ of 0.05 to 0.10) can be used, particularly if a greater amount of photobioreactors are to be inoculated with a lesser amount of inoculant. If the photobioreactor batch is grown for a longer term, such as 30 days or more, the low inoculum density may not have a considerable affect on product production. Thus, a low cell density inoculum can, in some situations, be somewhat less expensive overall, since more photobioreactors can be inoculated per inoculum batch.

A larger cell density inoculum can also be used, if desired. This may be preferred when a short lag phase is desired, or during shorter culture runs where product production will be higher if the inoculation density is higher. The choice of inoculation density can also be determined by the light intensity. Some strains may not tolerate high light intensity at low inoculation density, possible causing cell death or a longer lag phase before the growth phase.

Optical density (OD) is a measure of optical absorbance, typically using a spectrophotometer. Optical density (OD) is the absorbance of an optical element for a given wavelength $\lambda$ per unit distance. If OD is e.g. measured at wavelength 750 nm it may be referred to as $OD_{750}$. Measuring the optical density of a sample is an indirect method of determining the number of cells present. The amount of light of a specific wavelength that is absorbed by a culture is related to the number of cells. Thus, the OD measurement can be used as a simple and fast method of determining the cell count in a culture. The measurement of $OD_{750}$ of a culture correlates with cell growth, culture biomass, wet weight of a culture, and dry weight of a culture. The OD measurement can also correlate with the cell count per volume. However, it is often more feasible to simply measure $OD_{750}$ as an estimate of cell density than to utilize any of these other methods.

The optical density (OD) at 750 nm is used as a parameter for the cell density of cyanobacterial cultures. This measurement is based on both absorbance and on the light scattering of particles (the cells) in solution. As opposed to a measurement purely based on absorbance, the measurement of light scattering in a spectrophotometer is device-dependent—differences in the optics of different photometers result in different values. A commercially available turbidity standard can be used to standardize the $OD_{750}$ measurement of different spectrophotometers. One type of commercially available turbidity calculation standard is the Formazin Turbidity Standard (Sigma, TURB4000). Example 5 demonstrates how a turbidity standard can be used to standardize $OD_{750}$ over a number of spectrophotometer types.

The wavelength of OD that is measured can vary somewhat, but the OD at 750 nm is likely to be responsive to differences in cell density, but not other factors such as the amount of chlorophyll or carotenoids in a given culture.

Regarding the cyanobacterial culture, it is desirable that the scale-up culture is axenic—that is, free from other strains or other organisms, such as bacteria or fungi. In an embodiment, the culture is a pure culture of genetically modified cyanobacteria. An axenic culture can be scaled-up without contamination, the cell growth can be faster, and the product that is produced can accumulate at higher levels because it isn't consumed by the contaminant. Thus, in an embodiment, in order for the growing cyanobacterial cultures to be axenic or substantially axenic, particularly throughout multiple culture transfers, the components of the system (containers, medium, connectors, etc.) are treated so that they are substantially free from contaminants.

In an embodiment of the invention, all of the components of the system are sterilized, so that organisms other than the genetically enhanced cyanobacterial cells in the system are not present or are present at very low levels. The components of the scale-up system, such as flasks, nutrients, liquids, containers, connectors, pumps, etc. are sterilized in a suitable manner. The choice of sterilization method can depend on costs, residual residue that may be toxic to the cyanobacteria, heat or chemical stability of the materials, and effectiveness of the sterilization method. The components so sterilized can be "sterile"—that is, a completely free of live organisms. Alternatively, the sterilization process can be "substantially sterile"—that is, a small amount of live organisms may remain, but the bulk of the contamination has been removed. In some situations, such as sterilization-in-place of outdoor tubing with chemical sterilants, the complete removal of all organisms is difficult, but the remaining small amount of organisms does not pose a problem for the cyanobacterial culture.

Containers can be sterilized, for example, by autoclaving, by ozonation, by gamma irradiation, etc. Additionally, a wide range of suitable sterilizing solutions may be used to sterilize portions of the system. Basically, any solution suitable to sterilize or disinfect a surface can be used. In an embodiment, the solutions are biological oxidants. In an embodiment, the sterilizing solutions are halogen containing compounds, such as, for example, chlorine dioxide, bromine oxide, bromine chloride, monochloroamine, bromic acid, hypochlorous acid, chlorates, chlorites, hypochlorites, iodine monochloride, iodine trichloride iodine monobromide, etc. Combinations of two or more suitable compounds can also be used.

Further, the limited number of connections that are made, disconnected, and connected again during this process helps to mitigate the likelihood of introducing contaminants into the system.

The culture medium can be a fresh water medium or a salt water medium, depending on the organism. In an embodiment, the medium is MBG-11 medium, but other medium types can be used. The liquid (fresh water, brackish water, or seawater) to be used for the culture can be sterilized along with or separately from the medium components.

Medium components are typically sterilized by autoclaving. Larger amounts of liquid can be sterilized by filtration, steam treatment, ozonation, or autoclaving. However, any suitable, effective means for sterilizing the medium in a way that doesn't cause toxicity to the cyanobacterial cells once they are added can be used.

The sterile medium for each of the steps can be added either before the inoculum is added, or it can be added to the container after the inoculum is added. Alternatively, the appropriate amount of water (either fresh water, salt water, or brackish water) can be sterilized separately from the nutrient mix, and the two are added to the new culture container, either before, during, or after the addition of the axenic culture.

In some instances, it is more efficient to sterilize medium in a larger size container, and then transfer a small portion of it to the smaller container. When the smaller container is inoculated and allowed to grow to a desired OD, this volume can be transferred back to the remainder of the liquid in the larger container, to be allowed to grow to a desired OD, before being transferred to the next step. In this way, one less connection is made, thus there is a lower risk for contamination. For example, a larger amount of medium (such as 500 liters) can be sterilized in the third scale-up container that has previously been connected and sterilized together with the smaller container (such as 80 liters). In this example, 70 liters of sterile medium from the 500 liter container is transferred to the smaller container, 10 liters of inoculum is added, and the culture grows to a desired density. Then, the 80 liters of culture is inoculated into the 500 liter container by moving it back through the same sterile connection.

The connecting tubing that can be used is preferably thermoplastic tubing that can be autoclaved, is ozone resistant, and can withstand the wear of a peristaltic pump. In an embodiment, tubing material such as flexible PVC, Santoprene™ thermoplastic vulcanizate (TPV), C-Flex®, can be used.

In an embodiment of the invention, the parallel closed photobioreactors are suspended vertical photobioreactors made of a transparent or translucent flexible film, and supported, for example, by a metal or wood support structure. These photobioreactors can be made to a suitable height, length, and width, as desired. A heat sealing apparatus can be used to form the edges of the photobioreactor.

In another embodiment, the parallel closed photobioreactors are horizontal bags made of transparent or translucent flexible film. These photobioreactors can be laid on the ground directly, or on a platform.

In an embodiment, a pressure compensation flow control device 615 is placed upstream of each of the plurality of photobioreactors 609 so that a similar amount of inoculum can be transferred to each photobioreactor. In an embodiment, drip emitters are used for this purpose. Exemplary drip emitters include, for example, pressure compensating drip emitters made of ozone-resistant material that have a pressure range between 5-60 PSI and a liquid flow rate between 0.5- and 5 GPM. Drip emitters of various sizes and materials can be obtained from irrigation supply stores. An example of a drip emitter is the Rain Bird XB-05PC ½ gph Xeri-Bug Emitter (Barb Inlet), or the DIG 06-011 FC0-10 GPH Adjustable 8 Stream Drip Emitter ¼ in. barb, both of which are available on the world wide web at sprinklerwarehouse.com. Preferably, the drip emitters are made of a material that is sterilizable. In an embodiment, the drip emitters are re-used multiple times, with a sterilization procedure between each use.

The types of pumps that can be used to provide positive pressure without exposure to atmosphere include, for example, positive displacement pumps, such as peristaltic pumps, diaphragm pumps, piston pumps, and the like. Preferably, the chosen pump can withstand multiple sterilization passages, such as by steeping with a sterilant or ozonation.

Relative to US published application 20100304456, which teaches an inoculum equal to more than 5% of the carrying capacity of the final system, the present invention teaches as low as 1%. Further, with initial $OD_{750}$ of as low as 0.1, the present invention can achieve a doubling time of as low as 9 hours, and on average 12-14 hours.

EXAMPLES

Example 1

Preparation of Contamination Test Medium ("Cc Liquid Broth") and Solid Test Plates The contaminant test medium ("CC liquid broth") was prepared as follows: To 500 mL filtered seawater, the following chemicals were added: 1 g peptone, 1 g yeast extract, 1 g glucose, 1 g sucrose, and 1 g amicase. The mixture was stirred until completely dissolved, then autoclaved at 121° C. for 30 minutes. The solution was then cooled to room temperature. Then, 20 mL of sterile 50× BG-11 and Sodium Thiosulfate Pentahydrate stock was added to the solution using a UV laminar flow hood.

Solid plates containing the contaminant test medium were prepared as follows: In a one liter bottle with a stir bar, 10 grams of Bacto Agar was added to to 500 mL of RO water, and autoclaved at 121° C. for 30 minutes, then cooled slightly. The sterilized cc liquid broth (above) was mixed in under sterile conditions inside a laminar flow hood, and plates were poured in a UV laminar flow hood. Plates were cooled and stored at 4° C. until ready for use.

Example 2

Quality Control of CC Plates

For a positive control of contaminated test plates, a CC agar plate was placed on the laboratory bench top with the lid off for 10 minutes at room temperature. The lid was then placed back on the plate, the plate was wrapped with 3M micropore tape, and the plate was incubated at 30° C. for one week. In a typical test run, contaminant growth (presence of colonies) on this positive plate was observed within 2-3 days. In situations where no contaminants were observed with this positive control, the positive control failed, the CC plates were discarded, new CC plates were prepared, and the method was performed again until positive colonies were observable.

Example 3

Validation of Sterility Measures of Containers, Pumps, Tubing, Etc. Prior to Contact with the Cyanobacterial Cultures Each step and component in the scale-up system was sterilized by some means. Smaller volumes of liquid and smaller sizes of tubing, connectors, and containers, were sterilized using an autoclave. When larger amounts of culture medium were used, the master nutrient mix was sterilized using an autoclave and added to well water that had been previously sterilized by other means (such as ozonation). The tubing, pumps, emitters, and connections were sterilized by either autoclave, ozonation, steeping in a sterilant, or by other suitable means. Each of these steps was initially validated to confirm that the method resulted in contaminant-free components. The steps were also checked intermittently throughout scale-up to confirm the lack of contaminants.

In order to validate the sterility of the various methods, a sample sterilized component was contacted with CC broth for 2 days to 1 week at room temperature. Cloudy CC broth indicated that the sterilization process was not complete. Clear CC broth indicated that the sterilization process was successful.

Example 4

Testing for Contamination of a Cyanobacterial Culture Using the CC Plates

CC agar plates stored at 4° C. were warmed to room temperature. One drop (40 to 80 µl) of culture was streaked across a CC agar plate using a sterile loop tool inside a laminar flow hood. The plate was then wrapped with 3M micropore tape and incubated at 30° C. for one week in the dark. Contamination, when present, was typically observed within 1-2 days. Inoculum cultures that were found to be positive for either bacterial or fungal contamination were discarded.

Outdoor photobioreactors were then tested at inoculation and intermittently during the production period. While some minorly contaminated cultures were able to make product with no observable decrease in output caused by the contamination, other cultures were more fully contaminated, and were then discarded.

Example 5

Standardization of $OD_{750}$ Measurement Using Different Spectrophotometers

As mentioned earlier, the $OD_{750}$ measurement can differ when different spectrophotometers are used, particularly since it is a measurement of light scattering rather than absorbance. To standardize the $OD_{750}$ measurements across several different spectrophotometers, a commercially available turbidity standard, Formazin Turbidity Standard (Sigma, TURB4000) was used. Several different dilutions of the standard were made, as shown in Table 1, below (n=10). The Formazin standard was pre-diluted 1:2 with dd water prior to the dilutions shown in Table 1. The dilutions were measured in 5 different types of spectrophotometer.

TABLE 1 dilutions of the pre-diluted Formazin standard

| Dilution factor | Formazin standard 2000 NTU | dd water (particle free) |
| --- | --- | --- |
| 0.25 | 500 µl | 500 µl |
| 0.225 | 450 µl | 550 µl |
| 0.2 | 400 µl | 600 µl |
| 0.175 | 350 µl | 650 µl |
| 0.15 | 300 µl | 700 µl |
| 0.125 | 250 µl | 750 µl |
| 0.1 | 200 µl | 800 µl |
| 0.075 | 150 µl | 850 µl |
| 0.05 | 100 µl | 900 µl |
| 0.025 | 50 µl | 950 µl |

From the resulting measurements, conversion factors were determined for each type of spectrophotometer in order to standardize them to one selected spectrophotometer (Shimadzu UV-2450) to ensure the comparability of all optical density measurements, using the following calculation:
Calculation of Conversion Factors:
 Linear regression applied [b=0 (regression forced through point (0,0))]:
  y1=m1x (UV-2450)
  y2=m2x (test Spec)

To make the test spec value (y2) equal the UV-2450 value (y1)

$$y1=(m1/m2)*y2$$

Where (m1/m2)=the conversion factor

The slopes of the optical density values versus the dilution factors were calculated for the linear range, using the seven measurements from dilution 0.025 to 0.175. For the calculation, the regression was forced through zero. The slopes were then related to that of the UV-2450 results, and factors for conversion were calculated. The factor allows the conversion of $OD_{750}$ values measured with different spectrophotometers to the $OD_{750}$ value measured with the UV-2450 (Shimadzu) spectrophotometer, which was defined as the standard.

TABLE 2

Calculated conversion factors for $OD_{750}$ using various types of spectrophotometers

| Spectrophotometer Type | Conversion factor |
| --- | --- |
| Shimadzu UV-2450 | 1.000 |
| Shimadzu UV-1800 | 1.236 |
| NovaSpec Plus 1 | 0.766 |
| NovaSpec Plus 2 | 0.901 |
| GENESYS 10S | 1.545 |
| Beckman Coulter Inc. DU 730 | 1.426 |

Note that the $OD_{750}$ measured in the Examples herein have not been corrected with the standardization multiplier. The values listed in the Examples are raw values from a Thermo Fisher Scientific Genesys 20 Visible Spectrophotometer, model 4001/4). Using methods shown in this example, one can standardize the $OD_{750}$ of any spectrophotometer to a given standard so as to have a consistent standardized $OD_{750}$ when using different spectrophotometers.

Example 6

Sequential Scale-Up of Inoculum

The initial inoculation of the inoculum scale-up system is performed in a sterile laminar flow hood by transferring 100 mL of culture into a 1 L bottle in the scale-up system, using a sterile pipet. This culture is then diluted with sterile MBG11 media until there is approximately 600-900 mL in the bottle. All further transfers are performed according to inoculum scale-up system protocols (i.e. pressurization of culture bottle or media bottle and opening of valves without breaking the sterile envelope).
Transfer to 5 L bottle In the 1 L bottle, there will be approximately 900 mL of culture. When this volume reaches an ideal optical density at 750 nm ($OD_{750}$) of 4.0 (or higher, provided the culture is not in stationary phase), it is transferred to the previously connected three 5 L bottles. Each 5 L bottle receives 300 mL of inoculum. The 5 L bottles are then topped with 2 L of MBG11, from the previously attached sterile media carboy. This top-off results in an $OD_{750}$ of approximately 0.6. When this 2 L of culture reaches an $OD_{750}$ of 2.0, it receives another 2 L of media (resulting in a final volume of 4 L at $OD_{750}$ of 1.0). The media may be varied to extend exponential and linear growth phase such that the optical density at 750 nanometers can exceed 4.0.
Transfer to 80 L Flat Panel Reactor When the culture in a single 5 L bottle reaches an $OD_{750}$ of 3.0 (or higher, provided the culture is not in stationary phase), it is transferred into an 80 L reactor by fusing the tubing on the bottles and the reactor with the sterile tube fuser. 20 L of media is then added (also using the sterile tube fuser) for an $OD_{750}$ of 0.5. When this volume reaches an $OD_{750}$ of 2.0, an additional 20 L of media is added for an $OD_{750}$ of 1.1. Once again, when this culture reaches an $OD_{750}$ of 2.0, it receives the final 40 L of media ($OD_{750}$ of 1.1).

Transfer to 500 L Reactors

When the 80 L reactor reaches an ideal $OD_{750}$ of 3.5, it is transferred into a 500 L reactor by means of the sterile tube fuser with 420 L MBG11 media (resulting in an $OD_{750}$ of 0.6).

Transfer to 4,500 L Reactors

When a 500 L reactor reaches an $OD_{750}$ of 4.5, it is transferred to a 4,500 L commercial photobioreactor with the additional 4,000 L of MBG11 media (final $OD_{750}$ of 0.5).

Example 7

Protecting Inoculum from Contamination

In previous work, the transfer of inoculum into 1 liter and 5 liter containers was done in a fume hood, which required extra time and space. The repeated need to use the fume hood represented a bottleneck in the process of growing up inoculum. Furthermore, more frequent manipulations increased the risk of contamination. One has to do work sterilely, and any time one opens up a flask there is always a risk of contamination.

In one embodiment, depicted schematically as a system in FIG. 1, the one liter bottle and the five liter bottles are autoclaved as an interconnected system. The 20 liter carboy is autoclaved separately, but then connected aseptically to system in the hood or by sterile tube-fused connections outside of the hood. There is a transfer of the initial inoculum, in the hood or by sterile tube-fusing, to the one liter container. All connections are made and removed in the hood, which can be mobile, or by remote sterile tube-fused connections. Ports are sprayed with ethanol and opened under flame from a portable burner. An alternative is to steam the ports. With the use of the sterile tube fuser, no further work is done in the hood after the initial 100 mL culture volume added to the 1 L bottle.

Pressure from a pump is used to move liquid media. Excess gas volume leaves the system through an outlet port fitted with a 0.2 micron filter, so that no bacteria can enter the system. There is a sterile input port, which allows input of compounds such as vitamin B-12 and neomycin. There is a sterile sampling port in the 1 liter and 5 liter vessels to remove liquid samples, under pump pressure, so that one may determine the optical density of the inoculum culture. As the cell density increases within the 1 liter container, sterile sea water liquid is moved from the carboy to the 1 liter container to top off the liquid level in a way to maintain a desired optical density. As the liquid volume within the 1 liter container approaches 1 liter (generally around 900 mL), the inoculum from the 1 liter container is moved via pump pressure to the five liter container.

The inoculum is allowed to grow in the 5 liter container, with addition of media via pump pressure done in a way to roughly maintain a desired optical density. This optical density can be less than 1.0 for higher growth rates.

There is a sterile tube fuser which allows transfer of inoculum culture from the 5 liter container to an 80 liter container. The liquid level is topped off to maintain a desired optical density. There is a sterile tube fuser which allows transfer of inoculum culture from the 80 liter container to a 500 liter container.

In further embodiments, there are a plurality of one liter containers operationally connected to a plurality of 5 liter containers operationally connected to a plurality of 80 liter containers operationally connected to a plurality of 500 liter containers.

Example 8

Staged Inoculum Up to 4,500 Liter

Using the procedure outline in Example 7, 900 mL of liquid was transferred to a 1 liter bottle. The 900 mL comprised 150 mL of culture and 750 mL of media and nutrients.

After obtaining an OD of 2.0, the 900 mL of culture was transferred via pumping according to Example 7 into two 5 liter bottles with 2 liters of media in each. When the OD within the 5 liter bottles reached 1.5, another liter of media was added to each bottle. When the OD once again reached 1.5, an additional 2 liters of media was added to each 5 liter bottle, for a total volume of 4 liters in each bottle.

After obtaining an OD of 3.0, the 8 liters of culture was transferred via pumping according to Example 7 into 20 liters of natural salt water within an 80 liter bioreactor supported on a frame. Each time the OD reached 2.0, the volume was doubled until there were 80 liters in the reactor.

After obtaining an OD of 2.5 in the volume of 80 liters, the culture was transferred via pumping according to Example 7 into a bioreactor of volume 200 liters, which had sequential media additions until a final volume of 500 L was reached.

After obtaining an OD of 5.0 in a volume of 500 L, the culture was transferred into a bioreactor of volume 4,500 liters.

The 1 liter, 5 liter, and 80 liter containers used 1% $CO_2$ as a carbon source for growth. The larger containers utilized 1.75% $CO_2$. The 1 liter, 5 liter, and 80 liter containers were cultivated in a greenhouse. The added liquid comprised of BG-11 (with 3 µM EDTA) and $Na_2CO_3$ (20 mg/Liter)+ $K_2HPO_4$ (40 mg/Liter).

Example 9

Another Example of Inoculum Stain Up to 4,500 Liter

Using the staging of inocula in a manual procedure and similar to the outline in Example 6, 600 mL of liquid was transferred to a 1 liter bottle. The 600 mL comprised 100 mL of culture and 500 mL of media and nutrients.

After obtaining an OD of 2.5 or up to 4.0, the 600 mL of culture was transferred via pumping according to Example 6 into 10 liters of natural salt water within an 80 liter bioreactor supported on a frame. The 10 L culture volume was subsequently topped-off to 80 liters with sterile salt water and nutrients over the course of 5 days, while maintaining the OD at levels between 0.5 to 1.0.

After obtaining an OD of 1.0 in a volume of 80 liters of culture, the 80 L volume of inocula was transferred via pumping according to Example 6 into a bioreactor of volume capacity of 500 liters at an OD containing 100 liters of sterile seawater and media. The total volume of 180 liters with a final OD ranging between 0.2 to 0.5. After obtaining an OD of 1.0 in the initial volume, the initial volume was subsequently topped-off to 500 liters of sterile salt water and nutrients over the course of 7-10 days, while maintaining the OD at levels between 0.5 and 1.0.

After obtaining an OD of 2.5 in a volume of 500 liters of culture, 500 L of culture is transferred into a 4,500 liter bioreactor.

The 1 liter and 80 liter containers used 1.2% $CO_2$ as a carbon source for growth. The larger containers utilized 1.75% $CO_2$. The amount of $CO_2$ is dependent on the restriction of the diffuser and the height of the water column. The 1 liter and 80 liter containers were exposed to light from Spectralux T5 fluorescent 54 W (about 100 PAR at initiation 0.1 to 0.25 OD; and 400 PAR at OD 2.5 or greater). The added liquid comprised BG-11 (with 3 µM EDTA) and $Na_2CO_3$ (20 mg/Liter)+$K_2HPO_4$ (40 mg/Liter) 15 mg/L $NaNO_3$.

Example 10

Relating to Inoculation of Multiple Bioreactors

Treatment with Sterilizing Gas

Groups of bioreactors is preferably designed so that a sterilizing gas (such as ozone) can be supplied to all components of the system including each bioreactor and associated piping.

The piping systems are preferably free of dead ends and each system should end in a 0.2 µm filter so that the sterilizing gas (e.g., ozone) can be drawn across the entire internal surface of each system. Points where sterilizing gas will be added to the system should be identified and filters sized appropriately to ensure a consistent flow of 25 LPM with less than a 5 PSI pressure drop at these inlet points.

As a general matter, contamination can be controlled with the use of ozone. As to liquid water, this can be done by injecting concentrated ozone gas into process seawater. As to bioreactors and process lines in need of control, this can be done by treatment with humid ozone gas. Initially obtained sterility can be maintained by keeping the system isolated by 0.2 µm air filters during liquid transfers.

As to sterilization of seawater by ozone, the TRO [total residual oxidant] content of seawater will degrade from about 10 to about 0 in about 1 to 4 days, depending upon factors including liquid volume, light intensity, and temperature. The TRO of treated seawater should be sufficiently low so as not to interfere with the inoculation process, and preferably about zero. As a practical matter, ozone treated seawater should be allowed to stand so that TRO can decay for no less than 48 hours before inoculation.

Further as to the use of ozone, pressure must be maintained between 5 and 30 psi in the ozone generator to maintain its functionality. Flowpaths in the seawater sterilization system must be aligned and checked to ensure that pumps do not work against closed valves.

Example 11

Relating to Inoculation of Multiple Bioreactors

Use of a Manifold

A manifold can be used to connect multiple photobioreactors (PBR) in series (i.e., header) for inoculating each PBR from a single source culture and making a single connection to each reactor.

Separately, a manifold may be used in reverse for connecting multiple source cultures; however, a homogeneous stream is not made and tubing diameters must be considered.

The term manifold can reference a series of connections for linking more than one vessel to a single line that can be used for splitting a large volume of liquid (or gas) into multiple smaller vessels or conversely, combining multiple small source volumes into a larger reservoir. By connecting multiple vessels to a single line, there is only one connection made to the PBR at time of inoculation.

Example 12

Relating to Inoculation of Multiple Bioreactors

Use of a Mixing Chamber

Inoculation of research and commercial photobioreactors requires a large volume or biomass of potentially axenic cyanobacteria culture. In order to meet the volume or biomass demands, multiple cultures are often mixed together into a single chamber or linked together in series. Processing a single chamber to meet the capacity of inoculum for sterility and cleanup is not always practical or feasible for the specific inoculation event. Linking cultures in series also is not ideal for creating a homogenous culture, largely due to inconsistencies in mixing ratios between the linked cultures. This embodiment describes a practice for and verification of using a mixing chamber for up to three source cultures to create a homogenous stream for inoculation of replicate photobioreactors. More than three source cultures may be used as long as the combined tubing inner diameters (ID) of the mixing chamber (and source culture harvest line) exceed the mixing chamber outlet tubing ID.

The mixing chamber is positioned as an intermediate vessel between multiple source cultures that flow into the chamber through three separate inlets and an outlet vessel for depositing the mixed stream via a single outlet siphon. The outlet is connected to a peristaltic pump that draws head through the sealed mixing chamber, which creates a siphon from the source cultures at equal rates. The inlets extend further than the outlet siphon into the mixing chamber to allow for adequate mixing below the outlet siphon level. The multiple source cultures enter the mixing chamber via the inlet lines and become homogenized below the outlet siphon level. Once the chamber volume reaches the outlet siphon, the chamber contents are homogenously mixed and the outlet stream is an average of all source culture cell densities. For example, if three source cultures are being used with the following cell densities measured as $OD_{750}$: 1.0, 1.5, and 1.75, the average cell density of the mixed source cultures should be 1.42 $OD_{750}$. Using a 10 L carboy has yielded sufficient results in mixing three 80 L source cultures at varied cell densities into a single homogenous stream.

The outlet line can be any diameter and more inlets also can also be installed on the mixing chamber; however, the outlet diameter cannot exceed the maximum of a single inlet or the sum of tubing ID's of all inlets combined. The inlet lines are connected to the lid by barbed fittings forming a union through the lid to extend into the chamber from the underside of the lid. The inlet extension into the chamber is preferably longer than the outlet line that extends through the chamber. The inlet lines are preferably the same length, although slight variations (<1 cm) in the lengths have not shown to affect results significantly. The outlet line is connected to the barbed fitting on the lid with the largest diameter, and also to the transfer tubing used in the peristaltic pump. The pump draws from the single outlet line coming out of the mixing chamber. The pump drawing force on the siphon tube with a larger diameter than the combined source culture harvest lines (i.e., inlet tubes) provides enough force to siphon from multiple source cultures. The source culture harvest line and mixing chamber inlet tube IDs should match; however these may be different as long as the maximum siphon tubing ID does not exceed the combined inlet tubing ID's and the chamber inlet IDs are not greater than the source culture harvest line IDs.

Example 13

Relating to Inoculation of Multiple Bioreactors

Use of a Surge Tank

In order to connect inoculum and nutrients to multiple bioreactors, one may employ an inoculation/nutrient delivery header along with a surge tank. Such a system can comprise a diaphragm pump and a sequence of valves and piping that can direct liquid flow to and from a surge tank (recirculation) through a variety of paths. This recirculation allows for equal liquid distribution to the reactors.

In one embodiment, the system consists of a fiberglass deck box and a polyethylene surge tank. The deck box contains the pump, piping and valves that allow for the directional control of liquid flow. The plumbing consists of ½ inch schedule 40 PVC, ½ inch PVC ball valves, ½ inch PVC unions, ½ inch schedule 80 threaded tees, ½ inch PVDF and polyethylene barbed fittings.

The surge tank sits external to the deck box and acts as the re-circulatory reservoir for liquid additions. All santoprene lines on the surge tank are equipped with 25 mm 0.22 μM PTFE Polyfilters; each has a terminal male luer fitting, a three inch section of ¼ inch silicone tube with a slide clamp, and a male luer fitting secured to the filters female luer end. The silicone tubing can be attached to santoprene via a barbed polypropylene reducer. All barbed fittings are cable tied in place. This filter and clamp arrangement allows air to be forced through the lines to clear any residual liquid without compromising the sterility of the system.

One may transfer sterile seawater to the surge tank using a peristaltic pump. One may use a diaphragm pump to transfer inoculum culture during the inoculum scale-up. On may use a diaphragm pump to transfer organisms into the surge tank.

Example 14

Scale-Up of a Strain of *Cyanobacterium* sp. ABICyano1 to a Plurality of Outdoor Photobioreactors A scale-up system for the simultaneous inoculation of 800 photobioreactors was developed and demonstrated. This system consisted of three stages of growth in liquid media before being distributed to the final outdoor photobioreactor. The initial inoculum was a 100 mL of culture of the strain *Cyanobacterium* sp. ABICyano1 (genetically enhanced to produce ethanol when induced) in a 250 mL flask, grown on a shaker table, using a 16 hours on/8 hours off light cycle with a light intensity of 100 μE $m^{-2}$ $s^{-1}$.

This was transferred to the "first stage container", which was a 5 L glass media bottle containing 4 L of culture, which was outfitted with santoprene tubing (⅜" ID ⅛" wall-thickness) for the purpose of using a sterile tube fuser to make a sterile connection for transfer to the next stage of growth. The light cycle for this stage was 16 hours on/8 hours off, with a light intensity of 100 μE $m^{-2}$ $s^{-1}$. The "second stage container" was a translucent, flexible plastic 80 L bioreactor that was housed in a metal and plastic frame and also includes santoprene tubing for transfer to the third stage. The "third stage container" was a flexible plastic 500 L reactor that was also housed in a metal and plastic frame and has a santoprene tubing line for culture input. The culture outlet of the 500 L reactor differed from the previous stage in that it consisted of 1" braided PVC tubing that was used to make the connection to the inoculum delivery system at the block of 800 reactors, where there was also a section of 1" braided PVC tubing.

At each stage, the OD was measured. Thermo Fisher Scientific Genesys 20 Visible Spectrophotometer, model #4001/4, using 1 cm cuvettes and set at an absorbance of 750 nm. The machine was automatically calibrated daily, and was also manually calibrated before each use with seawater that was used for the medium preparation. Culture samples were analyzed in an undiluted form until they reached an $OD_{750}$ of 0.5. Above that level, the samples were diluted as needed to keep the $OD_{750}$ below 0.5.

In this specific example of an inoculation of 800 photobioreactors from two 500 L reactors of genetically enhanced *Cyanobacterium* sp. ABICyano1 culture, there were two separate batches (batch A and batch B, below) that were grown up identically from the 250 mL flask stage to the 500 L reactor stage:

Batch A: Axenic *Cyanobacterium* sp. ABICyano1 culture was grown to an $OD_{750}$ of approximately 1.0 in a 250 mL flask and axenically transferred to an autoclaved 5 L media bottle using a laminar flow hood. The culture reached an $OD_{750}$ of 1.024 with a final volume of 4 L after 5 days of growth and was transferred to a gamma-irradiated 80 L vertical reactor. This transfer was completed using a sterile tube fuser to connect the santoprene tubing (⅜" ID, ⅛" wall-thickness) between the 5 L bottle and 80 L reactor and a peristaltic pump to transfer the culture from the 5 L bottle to the 80 L reactor. The culture reached $OD_{750}$ of 1.06 with a final volume of 44 L after 3 days of growth and was transferred to a gamma-irradiated 500 L vertical reactor using the same sterile tube fusing technique as the previous transfer. After 26 days of growth, the culture reached an $OD_{750}$ of 2.22.

Batch B: The same procedure was followed as for Batch A, above, except that the culture in the 5 L bottle reached and $OD_{750}$ of 0.97 before transfer, and reached an $OD_{750}$ of 2.096 in the 44 L container.

Batch A and Batch B, each with a final volume of 524 L, were transferred to a block of 800 vertical photobioreactors, each having a final volume of 18 liters (that is, 400 photobioreactors were inoculated from each batch).

Each 524 L reactor was then axenically connected to the inoculum delivery system on the 800 block by connecting the 1" braided tubing from the reactor to the inoculum delivery sytem and steeping the surfaces of tubing that were exposed to atmosphere with a liquid sterilant. The inoculum delivery system and the delivery pathway to the 800 reactors were previously sterilized by ozonation. After the tubing was sufficiently sterilized, culture was delivered to the 800 reactors simultaneously using a diaphragm pump and piping system consisting of PVC and HDPE piping.

The upstream tubing of each of the 800 photobioreactors was fitted with a drip emitter, as shown in FIG. 6 (Woodpecker Pressure Compensating Junior with Barb; Manufacturer's No. 21502-001400; Model #: 01WPCJL4; Length—1.378"; Depth—0.037"; Width—0.052"; flow of 1 gallon/hour when pressure is between 7-45 PSI). Delivery pressure was maintained between 15-20 PSI in order to facilitate flow through the emitters, which have a pressure requirement of 7 PSI and a flow rate of 4 GPH. The parameters for this scale-up and inoculum delivery to the multiple photobioreactors is summarized in Table 3, below.

TABLE 3

Bioreactor scale-up parameters for Example 14

| | 250 mL | 5 L | 80 L | 500 L | 800 Block |
|---|---|---|---|---|---|
| Bioreactor Info | Plastic flask | Glass media bottle | Flexible Plastic Reactor supported by metal/plastic frame | Flexible Plastic Reactor supported by metal/plastic frame | 18 L hanging vPBR |
| Type of Transfer Tubing to next stage | n/a | Santoprene 3/8" ID 1/8" wall-thickness | Santoprene 3/8" ID 1/8" wall-thickness | Braided PVC 1" ID | Braided PVC 1" ID up to Diaphragm pump, PVC and HDPE piping to vPBR's |
| Method used to Transfer to next stage | Biohood | Peristaltic pump | Peristaltic pump | Diaphragm pump | n/a |
| Method of Sterilization | Gamma-Irradiation | Autoclave | Gamma-Irradiation | Gamma-Irradiation | Ozonation |
| Light Cycle | 16/8 | 16/8 | Ambient light | Ambient light | Ambient light |
| Light Intensity | 100 µE/m²/s | 150 µE/m²/s | Ambient light | Ambient light | Ambient light |

| | Flask | 5 L | 80 L | 500 L |
|---|---|---|---|---|
| Batch 1 | | | | |
| OD @ Transfer | ~1 | 1.024 | 1.06 | 2.224 |
| Volume @ Transfer | 100 mL | 4 L | 44 L | 524 L |
| # of Days Grown Before Transfer | n/a | 7 | 5 | 26 |
| Batch 2 | | | | |
| OD @ Transfer | ~1 | 0.976 | 0.97 | 2.096 |
| Volume @ Transfer | 100 mL | 4 L | 44 L | 524 L |
| # of Days Grown Before Transfer | n/a | 7 | 5 | 26 |

After the delivery to the 800 photobioreactors was complete (approximately 30 minutes), the $OD_{750}$ values for the 10 reactors sampled were very similar with a minimal standard deviation of 0.01, as shown in Table 4, below.

TABLE 4

| Photobioreactor # | Starting inoculum $OD_{750}$ |
|---|---|
| 1 | .191 |
| 2 | .169 |
| 3 | .176 |
| 4 | .17 |
| 5 | .164 |
| 6 | .196 |
| 7 | .206 |
| 8 | .198 |
| 9 | .192 |
| 10 | .196 |

We claim:

1. A process for inoculating a plurality of closed photobioreactors connected in parallel, each photobioreactor having a volume from about 10 liters to about 100 liters, with a cyanobacteria genetically enhanced for formation of a target molecule, comprising the steps of:

a. growing an inoculum culture of the genetically enhanced cyanobacteria in a first container to an $OD_{750}$ of from about 1.0 to about 10.0 in a volume of from about 1 liter to about 10 liters of pre-sterilized medium;

b. transferring the inoculum culture in a sterile manner under pressure without exposure to atmosphere from the first container to a pre-sterilized second container;

c. growing the inoculum culture in the second container to an $OD_{750}$ of from about 1.0 to about 10 in a volume of from about 20 liters to about 100 liters of pre-sterilized medium;

d. transferring the inoculum culture in a sterile manner under pressure without exposure to atmosphere from the second container to a pre-sterilized third container;

e. growing the inoculum culture in the third container to an $OD_{750}$ of from about 2.0 to about 10 in a volume of from about 200 liters to about 1,000 liters of pre-sterilized medium; and f. transferring the inoculum culture in a sterile manner at a pressure of from about 5 to about 50 psi without exposure to atmosphere from the third container and a sterilized nutrient solution, to a plurality of pre-sterilized photobioreactors comprising a pre-sterilized liquid, wherein said pre-sterilized photobioreactors have inlet tubing comprising a drip emitter and are configured in parallel from the third container, wherein said drip emitter controls the culture flow so that each of the photobioreactors connected in parallel is inoculated at a substantially similar flow rate.

2. The process of claim 1, wherein the inoculum culture is axenic.

3. The process of claim 1, wherein the volume in the photobioreactors is selected to obtain a starting cell density of the photobioreactors connected in parallel that is from about $OD_{750}$ of 0.01 to about 0.5.

4. The process of claim 1, wherein the starting cell density of the photobioreactors connected in parallel is from about $OD_{750}$ of 0.01 to about 0.5.

5. The process of claim 1, wherein the inoculum culture in the second container is grown to a cell density of about 2 to about 4 $OD_{750}$.

6. The process of claim 1, wherein the inoculum culture in the third container is grown to a cell density of about 2 to about 4 $OD_{750}$.

7. The process of claim 1, wherein the inoculum culture in the third container has a volume of about 500 liters.

8. The process of claim 1, wherein the number of photobioreactors connected in parallel that are inoculated from one third container is from about 25 to about 2,000.

9. The process of claim 8, wherein the number of photobioreactors connected in parallel that are inoculated from one third container is from about 100 to about 1,000.

10. The process of claim 9, wherein the number of photobioreactors connected in parallel that are inoculated from one third container is about 400.

11. The process of claim 1, wherein each of the photobioreactors connected in parallel has a final culture volume of about 18 to about 60 liters.

12. The process of claim 1, wherein the closed photobioreactors are vertical bioreactors.

13. The process of claim 1, wherein the drip emitters are functional after multiple sterilization procedures.

14. The process of claim 1, wherein the medium is a fresh water cyanobacterial medium, a brackish water cyanobacterial medium, or a salt water cyanobacterial medium.

15. The process of claim 1, wherein sterilized medium from the third container is used to fill the second container with sterilized medium.

16. The process of claim 1, wherein the target molecule is ethanol.

17. The process of claim 1, wherein at least one of the transfers occurs when the inoculum is in an exponential phase of growth.

18. The process of claim 17, wherein all of the transfers occur when the inoculum is in an exponential phase of growth.

19. The process of claim 1, wherein at least one of the transfers occurs when the inoculum is in a linear phase of growth.

20. The process of claim 1, wherein the plurality of pre-sterilized photobioreactors are inoculated substantially simultaneously.

21. The process of claim 20, wherein the plurality of photobioreactors that are inoculated substantially simultaneously have a similar inoculum $OD_{750}$.

22. The process of claim 1, wherein the inoculum is distributed to the plurality of pre-sterilized photobioreactors in about 30 minutes to about an hour.

23. The process of claim 22, wherein about 400 photobioreactors are inoculated in about 30 minutes.

* * * * *